United States Patent [19]

Stiso et al.

[11] 4,108,727

[45] Aug. 22, 1978

[54] METHOD, COMPOSITION AND DEVICE FOR DETERMINING THE SPECIFIC GRAVITY OR OSMOLALITY OF A LIQUID

[75] Inventors: Sisto Nicholas Stiso, Elkhart, Ind.; Chester L. Sutula, Annandale, N.J.

[73] Assignee: Miles Laboratories, Inc., Elkhart, Ind.

[21] Appl. No.: 716,962

[22] Filed: Aug. 23, 1976

[51] Int. Cl.$^2$ ............................................. G01N 31/14
[52] U.S. Cl. ..................... 195/103.5 R; 195/103.5 C; 195/103.5 UR; 195/127; 23/230 B; 23/253 TP; 426/231
[58] Field of Search .................... 195/99, 103.5 R; 23/230 B, 253 TP; 73/32 R, 64.3; 426/231

[56] References Cited

U.S. PATENT DOCUMENTS

| | | | |
|---|---|---|---|
| 3,447,904 | 6/1969 | Rupe | 23/230 B |
| 3,791,988 | 2/1974 | Josef et al. | 23/253 TP |
| 3,873,269 | 3/1975 | Kraffezyk et al. | 23/253 TP |
| 3,948,730 | 4/1976 | Gagnon et al. | 195/103.5 R |
| 4,015,462 | 4/1977 | Greyson | 73/32 R |

OTHER PUBLICATIONS

Chang et al., Canadian J. of Physiology and Pharmacology, vol. 44 (1966), pp. 115–128.

*Primary Examiner*—Alvin Tanenholtz
*Assistant Examiner*—C. A. Fan
*Attorney, Agent, or Firm*—Edward H. Gorman

[57] ABSTRACT

A method and device for determining the specific gravity or osmolality of a liquid containing a nonionic, ionizable solute are disclosed. The method comprises contacting the liquid with an ionizing agent, thus converting the solute to ionized species in the liquid, and contacting the liquid with test means capable of producing a detectable response, such as a color response, dependent upon the specific gravity or osmolality of the ionized liquid. The composition comprises an ionizing agent capable, upon contact with the liquid, of ionizing the solute therein, and a test means capable, upon contacting the liquid containing the solute in ionized form, of producing a detectable response which is a function of the specific gravity or osmolality of the liquid. The device comprises a carrier matrix incorporated with the test means and the ionizing agent.

35 Claims, 2 Drawing Figures

EFFECT OF UREASE ON DYE RELEASE FROM
MICROCAPSULES IN AQUEOUS UREA SOLUTIONS

FIG. I

VARIATION IN PERCENT REFLECTANCE WITH RESPECT TO UREA CONCENTRATION (TEST DEVICES)

METHOD, COMPOSITION AND DEVICE FOR DETERMINING THE SPECIFIC GRAVITY OR OSMOLALITY OF A LIQUID

BACKGROUND OF THE INVENTION

1. Field of the Invention

This invention relates to the determination of the specific gravity or osmolality of a liquid. More specifically, the present invention lends itself to accurate determinations of the specific gravity or osmolality of a liquid when nonionized solutes, such as urea and glucose, are present in the sample.

2. Description of the Prior Art

There are numerous arts in which it is useful to know the osmolality or specific gravity of a liquid. Such arts include brewing, urinalysis, water purification, etc. Needless to say, a quick, facile method for determining these parameters would greatly advance the state of many scientific disciplines, as well as any technology where rapid, accurate determination of these liquid characteristics would be beneficial. Thus, for example, if a medical laboratory technician could accurately measure these properties in urine samples in a matter of seconds, not only would a patient be afforded rapid results to aid the physician in diagnosis, but also laboratory efficiency would increase to a degree where many more analyses could be performed than were heretofore possible.

Although the present invention lends itself to a vast range of applications, for purposes of clarity this discussion will be couched largely in terms of the determination of osmolality or specific gravity of urine. Applications to other disciplines will become apparent from an understanding of how this invention relates to urinalysis.

The determination of urine osmolality is of considerable value in the understanding and clinical management of water electrolyte disturbances. Hence, complete urinalysis should, and usually does, include an osmolality determination.

Osmolality is a colligative property of a given solution, and is therefore related to freezing point, melting point, boiling point, vapor pressure, and osmotic pressure — also colligative properties. It is a function of the number of particles in solution, as opposed to their weight or density.

Osmolality is mathematically defined by the following relationship $$\text{Osm} = \phi nm$$

where Osm is the osmolality of a solution, $\phi$ is the dissociation constant of the solutes, $n$ is the number of dissociated ions per molecule of dissociated solute, and $m$ is the molality of the solution. Hence, as the solutes approach complete dissociation, $\phi$ approaches unity and the equation reduces to $$\text{Osm} = nm,$$

the equation for an ideal electrolyte.

Whereas a close correlation exists between osmolality and specific gravity in a solution containing a single solute, the correlation markedly diminishes in complex solutions containing nonionic species. Urine is a prime example of such a solution which deviates from ideal electrolytes. For example in one study urine specific gravities of 1.016 correspond to osmolalities ranging from 550 to 910 m Osm/kg. (T. Rodman, et al.; Journal of the American Medical Association: 167: 172, 1958).

Prior art methods for determining osmolality include the use of various commercially available osmometers which vary from manual to fully automated operation. For clinical work, however, freezing point measurement is usually chosen because of its relative simplicity. However, such procedures are fraught with many disadvantages. They are time-consuming, requiring steps of centrifugation to remove solids, super cooling below the freezing point, crystallization, and waiting for the temperature to rise to the actual freezing point.

Prior art methods for determining specific gravity utilize hydrometers, urinometers, pycnometers, gravimeters, and the like. Although these prior art procedures are satisfactorily sensitive, they all require fragile, bulky instruments which must be constantly cleaned, maintained, and calibrated to continuously assure their reliability. In addition, there are many inconveniences associated with the mechanics of using these instruments. There may be difficulty in reading the meniscus. Froth or bubbles on the liquid surface may interfere with the reading. There is a tendency for urinometers to adhere to the sides of the vessel containing the liquid sample. In the case of urine, the sample is frequently inadequate for floating a urinometer.

A recent breakthrough in which all of the above disadvantages have been virtually eliminated, and which affords extremely rapid osmolality determination, is disclosed in U.S. Ser. No. 647,416, filed by Greyson, et al. on Jan. 8, 1976 and assigned to the assignee of this application. Application Ser. No. 647,416 describes an invention in which a carrier matrix is incorporated with osmotically fragile microcapsules, the walls of which are composed of a semipermeable polymeric membrane material. Encapsulated inside the walls is a solution containing a coloring substance. When the capsules are in contact with a solution having a different osmolality than that within the capsules, an osmotic gradient is created across the capsule walls. This gradient causes solvent to permeate the capsule walls in the direction of the higher osmolality. Hence, if the internal liquid contains a higher number of particles per unit volume than the sample, solvent will flow into the capsules, tending to dilute their contents. Because of this phenomenon, the hydrostatic pressure within the capsules increases, causing swelling and/or rupture and the concomitant release of coloring substance. The rate and extent of release of the microcapsule contents is a function of the initial osmotic gradient across the capsule wall, and, hence, of the osmolality or specific gravity of the liquid external to the capsule. This technique is thoroughly described and taught in the above-cited patent application, which is hereby incorporated into the present disclosure by reference.

The microcapsule technique enables the laboratory technician to simply dip one carrier matrix into a urine sample, remove it, and observe any change in color. Hence, it can be seen that microcapsules represent a marked improvement over the art.

However, as stated supra, urine is a complex solution, containing nonionized solutes such as urea and glucose. When urine is contacted by the microcapsules, these molecules can permeate the microcapsule walls along with the solvent, thereby creating an inherent inaccuracy. It is to this problem of inaccuracy that the research leading up to the present invention was directed.

The fruits of that research provide a technique for measuring osmolality or specific gravity of a liquid containing nonionic solutes with a dramatically enhanced degree of accuracy.

BRIEF SUMMARY OF THE INVENTION

Briefly stated, the discovery comprising the present invention is a method, composition and device for determining the specific gravity or osmolality of a liquid containing a nonionic, ionizable solute. The method comprises contacting the liquid with an ionizing agent capable of ionizing the solute, thus ionizing the solute in the liquid; and contacting the liquid with test means capable of producing a detectable response, for example a color response, dependent upon the specific gravity or osmolality of a liquid containing the solute in ionized form. The intensity of the detectable response produced is a mathematical function of the property being determined and can be read by the laboratory technician. In the case of a color response, he merely observes the color and compares it with a color chart, the color intensity being a function of specific gravity or osmolality. The preferred device comprises a carrier matrix incorporated with a composition comprising at least one ionizing agent capable, upon contact with a liquid containing a nonionic ionizable solute, of ionizing the solute therein, and a test means capable upon contact with a liquid containing the solute in ionized form, of producing a detectable color response which is a function of the specific gravity or osmolality of such liquid.

BRIEF DESCRIPTION OF THE DRAWINGS

Other and further advantages and features of the invention will be apparent to those skilled in the art from the following detailed description thereof, taken in conjunction with the accompanying drawings, in which.

DETAILED DESCRIPTION OF THE INVENTION

Figure 1:
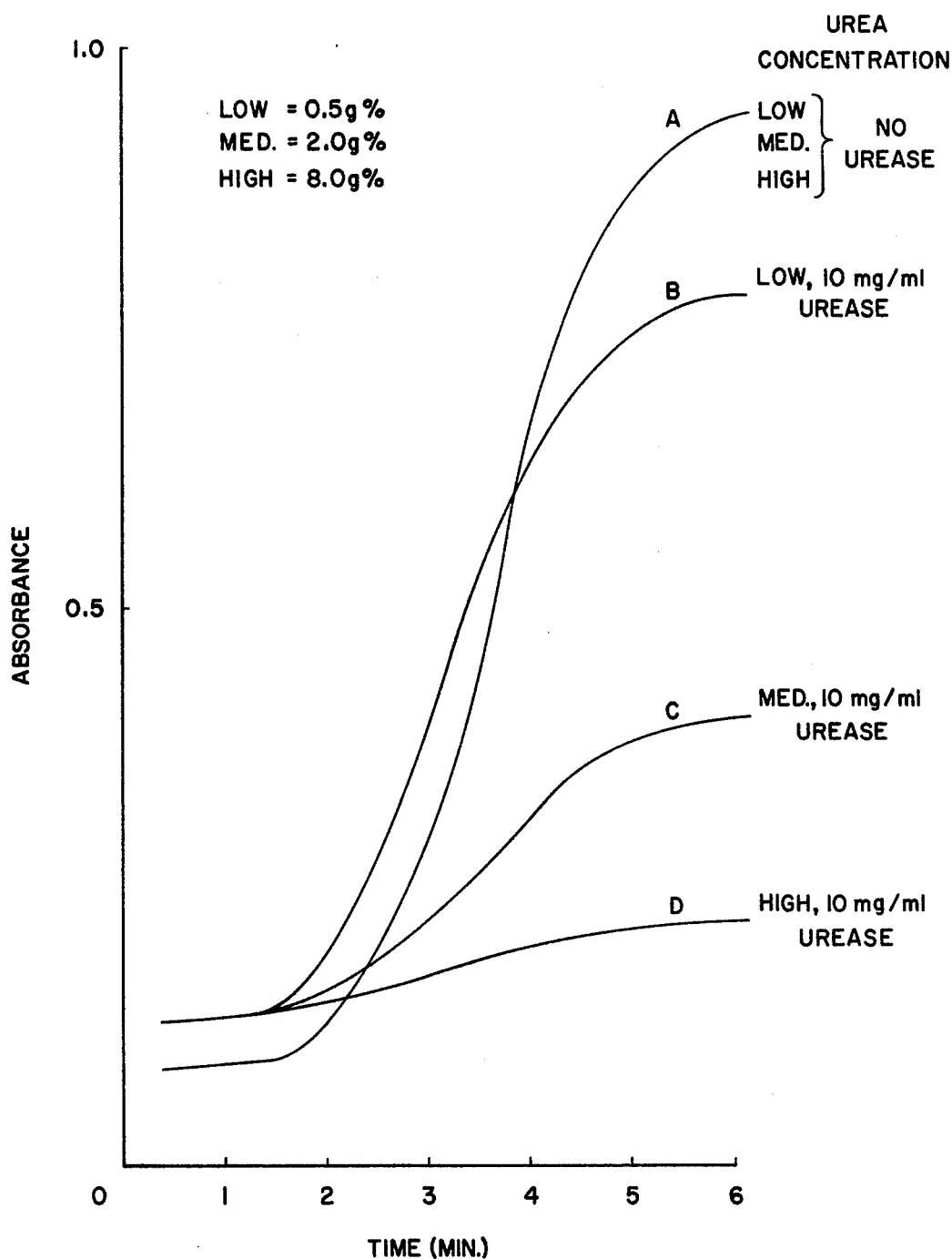
FIG. 1 is a graph plotting the effect of urease on dye release from microcapsules in aqueous urease solutions on the X axis against absorbence on the Y axis, with respect to various concentrations.

The greatly increased sensitivity afforded by the present invention resides, as stated supra, in the ionization of solutes which can interfere with the determination. Hence, in the case of urine, where nonionic solutes such as urea and/or glucose may be present, these substances are ionized such that when the liquid is contacted with the test means, the response of the test means will reflect the concentration of solute in the sample, including the nonionized solute initially present therein.

The ioniziation of these solutes is accomplished through the use of an ionizing agent. In general terms, this can be any means for converting the nonionic solute into ionic compounds, but usually a chemical or catalytic means is employed such as, in the case of urea, a hydrolyzing enzyme. Examples include urease and urea carboxylase (hydrolyzing). In the case of glucose, an ionizing agent such as glucose oxidase may be employed.

Although any suitable test means for producing a detectable response to the specific gravity or osmolality of the liquid can be employed in the present invention, the microcapsules in U.S. Ser. No. 647,416 (see above) are preferred. Hence, a preferred test means comprises at least an effective number of microcapsules containing a coloring substance which is released when the microcapsules are exposed to a certain osmotic gradient across the capsule walls. The walls of the microcapsules are osmotically fragile, semipermeable membranes, and the walls encapsulate a solute and a dye or dye precursor as coloring substance. Thus, when they are subjected to a pre-selected osmotic gradient across the walls, the microcapsules release the coloring substance.

The microcapsules can be prepared by a variety of well-known methods. Indicative of these is the method described in Angew. Chem. Internat. Edit., 14: 539 (1975) and the references cited therein. Techniques such as interfacial polycondensation, coacervation and the like will produce microcapsules. Other techniques such as centrifugation, spray drying, and other physiomechanical techniques will likewise find utility in preparing the microcapsules.

Interfacial polycondensation is a perffered method for making the microcapsules because of the relative ease it provides. In this technique two reactive species (comonomers or oligomers) are caused to react at the interface of a multiphase system. There, polycondensation occurs, forming a thin polymeric film which is insoluble in the media containing the monomers. Suitable microcapsules have been prepared by dissolving a first co-monomer component, such as a polyfunctional amine, in a aqueous phase containing the color substance. This aqueous phase is preferably a solution of a dye or dye precursor and a solute, such that the solution has a high specific gravity or osmolality relative to the expected osmolality range of the fluid to be analyzed. This aqueous phase is then dispersed or emulsified in a water immiscible phase such as mineral oil. A second co-monomer, such as a polyfunctional acyl halide, is then added to the suspension or emulsion. When the co-monomers are polyfunctional amines and acyl halides, polyamide microcapsules are formed, each of which contains a portion of the aqueous phase, i.e. coloring substance.

Suitable polymeric material useful to form the osmotically fragile, semipermeable membrane wall of the microcapsules include, in addition to polyamide, polyester, polyurethane, polyurea, and the like.

Suitable solutes used in the aqueous phase to define its osmolality should be soluble in the liquid to be tested. Hence, if the liquid to be tested is aqueous, such as urine, any suitable water soluble salt may be used. These would include organic and inorganic salts. Sodium chloride has been found to be particularly adaptable. The concentration of the solute can be widely varied to meet the intended analytical application. It is only necessary that the inner phase of the microcapsule possess a specific gravity or osmolality sufficiently greater than the liquid to be tested so that an initial osmotic gradient is established across the capsule wall upon contact with the sample liquid. It will be clear to one skilled in the art that the specific gravity or osmolality of the inner phase must be high enough so that at least some of the capsules will rupture upon contact with the sample solution, thus releasing the coloring substance.

Examples of coloring substances which may be used are alizarin, bromothymol blue, crystal violet, Evans blue dye, malachite green, methyl orange, Prussian blue, and similar dyes.

Also useful as a coloring substance are dye precursors which can react with complementary substances contained in the sample to be analyzed. For example, colors can be generated through diazonium couplings, oxidation, reduction, pH change, and other similar means. A preferred precursor is chromotropic acid, which upon release from microcapsules can combine with diazonium salts such as diazotized 2,4-dichloroaniline to produce a red color.

In a preferred embodiment of the invention, the above-described microcapsules, together with an ionizing agent, are incorporated with a carrier matrix and utilized as a dip-and-read type test device. This device may be prepared by various well-known methods which include impregnating an absorbent matrix with the microcapsules and an ionizing agent capable of ionizing non-ionic solutes contained in the sample to be analyzed. In the case where the sample is urine, the ionizing agent can be urease or urea carboxylase (hydrolyzing) and/or glucose oxidase. The latter enzyme will hydrolyze glucose, whereas the others hydrolyze urea.

Binders have been found to be useful in securing the microcapsules to the matrix. Among those found particularly desirable are cellulose acetate, cellulose acetate butyrate, hydroxy propyl cellulose, polyvinyl pyrrolidone. Binders which may be used are immiscible with the test sample and allow the sample to be absorbed into the carrier matrix.

Suitable absorbent matrices which may be used include paper, cellulose, wood, synthetic resin fleeces, glass fiber paper, polypropylene felt, non-woven and woven fabrics and the like. The impregnated matrix is advantageously affixed by any suitable means to a carrier member such as a polymeric strip, to facilitate use.

In the use of the test device, the impregnated matrix is immersed in the liquid to be tested, and immediately withdrawn. If the test liquid has a lower specific gravity or osmolality than that of the inner phase of the microcapsules, some of the solvent from the test sample will permeate the capsule walls, and the resulting increase in internal pressure will cause the release of the inner phase, thereby producing a color in the matrix. The color thus produced is then compared with precalibrated color standards to determine the specific gravity or osmolality of the test sample. The color standards are prepared using test liquids of known specific gravity or osmolality and test devices similar to those used in the analysis. In addition to visual comparison, various instrumental methods may also be employed to determine the nature of the color developed, thus obviating any subjective color determination associated with human observation.

It has been found that the instant devices are highly sensitive. Those prepared as presently described are capable of resolving 0.010 specific gravity units in the specific gravity range of about 1.000-1.050. They find particular utility in determining specific gravity and osmolality of such liquids as saline solutions and urine. Other specific gravity ranges can be determined by use of microcapsules having a suitable osmotic fragility and permeability and an internal phase of suitable specific gravity or osmolality. Hence, the microcapsule parameters can be easily adapted by one skilled in the art to fit a plurality of specific gravity and osmolality ranges.

The following examples are presented in order to further describe the present invention and to more clearly illustrate how it is made and used. It is to be understood, however, that the examples are in no way intended as limiting the scope of the invention.

A. Preparation of the Test Device

EXAMPLE 1 — Preparation of Microcapsules for initial liquid Suspension Studies

This example illustrates a typical method for preparing polyamide microcapsules for use as the color means of the present invention.

Into a flask were added
55 ml. mineral oil
25 ml. $CCL_4$
1 g. bentonite
3 μl. Sorbitan Trioleate (Span 85)
Into a first beaker were added
3 ml. 1M NaCl
0.4 g. NaOH
0.75 ml. ethylenediamine
0.75 ml. diethylenetriamine
0.5 g. Evans blue dye
Into a second beaker was added
6 ml. $CCl_4$
6 ml. n-pentane
3 ml. sebacyl chloride The aqueous solution in the first beaker was added to the contents of the flask with stirring, using a magnetic stirrer at its highest speed, for about 20 seconds. The stirring rate was then reduced to a speed just sufficient to prevent the dispersed phase from settling. Next, the contents of the second beaker was rapidly added to the flask. Stirring was continued for about 1 hour, whereupon solid microcapsules were removed from the reaction medium by filtration of the flask contents. The isolated capsules were then washed with petroleum ether and air dried. The resulting capsules were 20% > 500μ, 60% 250 to 500μ and 20% < 250μ in diameter.

EXAMPLE 2 — A preferred Preparation of Capsules

The procedure of Example 1 was followed except that:

The ingredients in the flask were
550 ml. mineral oil
400 ml. $CCl_4$
25 μl. Span 85 (Sorbitan Trioleate) purchased from Atlas Chemical Co.
11 g. bentonite
2.5 g. Syloid 65 obtained from W. R. Grace & Co.

The contents of the flask were stirred on a magnetic stirrer at relatively high velocity to assure maintenance of dispersion.

Into a first beaker were added:
50 ml. of a chromotropic acid solution.*
12 ml. diethylenetriamine
12 ml. ethylenediamine
10 g. NaCl

* The chromotropic acid solution was prepared by adding enough water to 65 g. NaOH and 10 g. of chromotropic acid to make 500 ml.

Into a second beaker were added:
60 ml. $CCl_4$
60 ml. n-pentane
30 ml. sebacylchloride
0.15 g. trimesoylchloride The aqueous solution in the first beaker was added to the contents of the flask with stirring, using a magnetic stirrer at its highest speed, for about 20 seconds. The stirring rate was then reduced to a speed just sufficient to prevent the dispersed phase from settling. Next, the contents of the second beaker was rapidly added to the flask. Stirring was continued for about 1 hour, whereupon solid microcapsules were removed from the reaction medium by filtration of the flask contents. The isolated capsules were then washed with petroleum ether and air dried. The resulting capsules were sieved, and those having diameters in the range of 90 - 125μ (microns) were collected.

EXAMPLE 3 — Incorporating the Composition with a Carrier Matrix

In this example, incorporation of the microcapsules of Example 2, an ionizing agent (urease) and a carrier matrix is illustrated.

As a carrier matrix, ICTOSTIX ® paper containing diazotized 2,4-dichloroaniline, obtained from Miles Laboratories, Inc. Elkhart, Indiana, was employed. The paper was cut into 0.2 × 0.4 inch strips. A 2% w/v (weight to volume) solution of hydroxypropyl cellulose in chloroform was prepared. Urease was suspended in the solution in an amount of about 20mg/ml (2000 International Units/ml), and the resulting suspension was homogenized by forcing it between a glass tube and a close fitting pestle of Teflon ® fluorocarbon resin manufactured by (E.I. duPont deNemours, Inc.). The urease was prepared from dried jackbean and was obtained from Product Research Division of Miles Laboratories Limited, Goodwood, South Africa.

One gram of the capsules from Example 2 was added to 10 ml. (milliliters) of the urease suspension and the resulting slurry was coated onto the paper containing the diazonium salt using a doctor blade adjusted to lay a wet film of 12 mils. The coated paper was then dried in an oven at 67° C. for about 3 minutes, thus leaving the urease and microcapsules incorporated with the matrix and hydroxypropyl cellulose.

B. The Effect of Urease on Sensitivity to Varying Urea Concentrations

EXAMPLE 4 — Control Capsules

Microcapsules were prepared in accordance with Example 1, and tested to determine the rate and extent of dye release under test conditions. About 25mg (milligram) of dried microcapsules were placed into 3 standard spectrophotometric curvettes. Three aqueous solutions of simulated urine were then prepared having normal physiological concentrations of NaCl and $PO_4^=$, but which contained varying concentrations of urea. The concentrations of NaCl and $PO_4^=$ were 10g/l. (gram per liter) and 2g/l., respectively, in each solution. The urea concentrations were 0.5, 2 (normal), and 8 gram percent.

About 3ml of test solution was added to a cuvette containing the microcapsules, and permitted to stand for 15 seconds. Each cuvette was then briefly agitated and placed in a Beckman DK-2a spectrophotometer. At 30 second intervals thereafter, the percent absorbance of the cuvette was measured at 575nm (nanometers) as a function of time. This data was plotted and it was found that variation of urea concentration did not measurably affect the results. This data is plotted in FIG. 1 as curve A.

EXAMPLE 5 — The Effect of Urease

The test solutions were next examined in the same fashion as in Example 4 except that the solutions contained 10mg/ml (1000 International Units/ml) urease. Each solution was incubated for 10 minutes to permit hydrolysis of urea. Each test sample was then placed in the Beckman spectrophotometer and percent absorbance of 575nm was recorded as a function of time. FIG. 1 shows the plotted data and curves B, C, & D represent low (0.5g%), medium (2.0g%), and high (8.0g%) urea concentrations, respectively. As can be seen from FIG. 1, the presence of urease caused significant differences in absorbance for differing urea concentrations, whereas no difference was observed absent urease.

C. The Effect of Urease in a Test Device

EXAMPLE 6 — Control Test Strip

Test devices were prepared as in Example 3 except that no urease was incorporated with the microcapsules and matrix. Three solutions of varying urea concentrations (0.5, 2 and 8 g percent) were prepared and a separate test device was wetted with each solution by pipetting 40μl of solution onto the matrix.

Figure 2:
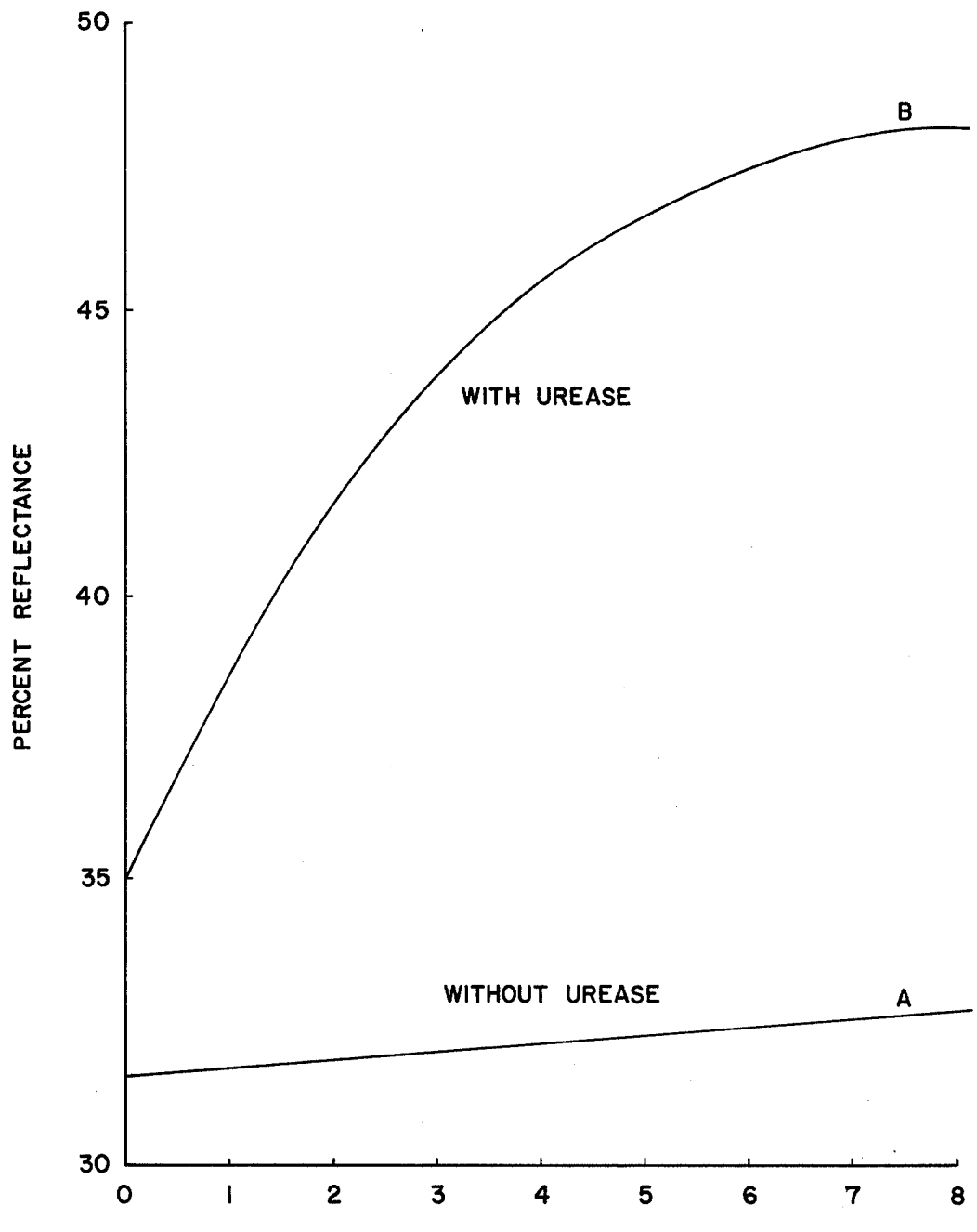
FIG. 2 is a graph illustrating variations in percent reflectance of test devices with respect to urea concentration in which urea concentration is plotted on the X axis and percent reflectance is plotted on the Y axis.

Each strip was then placed into an integrating sphere reflectance photometer and percent reflectance was measured at 580nm 1 minute after wetting. Percent reflectance was then plotted as a function of urea concentration (FIG. 2, curve A). There was little effect on percent reflectance, indicating the inability of the device to accurately portray the presence of urea in the test solution.

EXAMPLE 7 — Test Devices Containing Urease

Test devices prepared in accordance with Example 3 (i.e. containing urease) were tested in the same manner and with the same test solutions as in Example 5. Percent reflectance is plotted as a function of urea concentration in FIG. 2 (curve B). It can be seen that the presence of urease greatly enhances the sensitivity of the test devices to urea solutes. Hence the data dramatically illustrates the greatly improved accuracy in determining specific gravity ahd osmolality afforded by the present invention.

Obviously, many other modifications and variations of the invention as hereinbefore set forth may be made without departing from the spirit and scope thereof.

What is claimed is:

1. A method for determining the specific gravity or osmolality of a liquid containing a nonionic, ionizable solute, said method comprising
    contacting the liquid with an ionizing agent capable of ionizing said nonionic solute therein, and a test means capable, upon contact with a liquid containing said solute in ionized form, of producing a detectable response which is a function of the specific gravity or osmolality of such liquid, and
    subsequently determining the specific gravity or osmolality of the liquid by detecting the response produced by the test means.

2. The method of claim 1 wherein said test means produces a color response.

3. The method of claim 1 in which the test means comprises microcapsules containing a coloring substance, the microcapsules being capable of partially releasing the coloring substance to produce a visible color in response to a certain osmotic gradient across the microcapsule walls.

4. The method of claim 3 in which the solute comprises urea, glucose, or mixtures thereof.

5. The method of claim 4 in which the ionizing agent is urease or urea carboxylase (hydrolyzing) when the solute is urea, glucose oxidase when the solute is glucose, or urease or urea carboxylase (hydrolyzing) and glucose oxidase when the solute is a mixture of urea and glucose.

6. A method for determining the specific gravity or osmolality of a liquid containing urea, said method comprising contacting the liquid with a hydrolyzing agent capable of hydrolyzing the urea therein, and a test means capable, upon contact with a liquid containing urea in hydrolyzed form, of producing a detectable color response which is a function of the specific gravity or osmolality of such liquid, and subsequently determining the specific gravity or osmolality of the liquid by observing the color response produced by the test means.

7. The method of claim 6 in which the hydrolyzing agent is an enzyme capable of hydrolyzing urea.

8. The method of claim 6 in which the hydrolyzing agent is urease or urea carboxylase (hydrolyzing).

9. The method of claim 6 in which the hydrolyzing agent is urease.

10. The method of claim 6 in which the test means comprises microcapsules containing a coloring substance, the microcapsules being capable of partially releasing the coloring substance to produce a visible color in response to a certain osmotic gradient across microcapsule walls.

11. The method of claim 10 in which the hydrolyzing agent is an enzyme capable of hydrolyzing urea.

12. The method of claim 10 in which the hydrolyzing agent is urease or urea carboxylase (hydrolyzing).

13. The method of claim 10 in which the hydrolyzing agent is urease.

14. A composition for determining the specific gravity or osmolality of a liquid containing a nonionic, ionizable solute comprising in combination at least one ionizing agent capable, upon contact with a liquid containing the nonionic solute, of ionizing the solute therein, and a test means capable, upon contact with a liquid containing said solute in ionized forms, of producing a detectable response which is a function of the specific gravity or osmolality of such liquid.

15. The composition of claim 14 wherein the response produced by the test means is a color response.

16. A device for determining the specific gravity or osmolality of a liquid containing a nonionic, ionizable solute, the device comprising a carrier matrix incorporated with at least one ionizing agent capable, upon contact with a liquid containing said nonionic solute on ionizing said solute, and test means capable, upon contact with a liquid containing the solute in ionized form, of producing a detectable response which is a function of the specific gravity or osmolality of such liquid.

17. The device of claim 16 in which the response produced by the test means is a color reponse.

18. The device of claim 16 in which the means comprises microcapsules containing a coloring substance, the microcapsules being capable of at least partially releasing the coloring substance to produce a visible color response to a certain osmotic gradient across the microcapsule walls.

19. The device of claim 18 in which the ionizing agent is urease or urea carboxylase (hydrolyzing) and the solute is urea; or the ionizing agent is glucose oxidase and the solute is glucose.

20. A device for determining the specific gravity or osmolality of a liquid containing urea which comprises a carrier matrix incorporated with a hydrolyzing agent capable, upon contact with a liquid containing urea, of hydrolyzing the urea therein, and test means capable, upon contact with a liquid containing urea in ionized form, of producing a detectable color which is a function of the specific gravity of such liquid.

21. The device of claim 20 in which the hydrolyzing agent is an enzyme capable of hydrolyzing urea.

22. The device of claim 20 in which the hydrolyzing agent is urease or urea carboxylase (hydrolyzing).

23. The device of claim 20 in which the hydrolyzing agent is urease.

24. A device for determining the specific gravity or osmolality of a liquid containing urea which comprises a carrier matrix incorporated with microcapsules containing a coloring substance, the microcapsules being capable of at least partially releasing the coloring substance to produce a visible color response to a certain osmotic gradient across microcapsule walls, and a hydrolyzing agent capable of hydrolyzing urea in the presence of the microcapsules.

25. The device of claim 24 in which the hydrolyzing agent is an enzyme capable of hydrolyzing urea.

26. The device of claim 24 in which the hydrolyzing agent is urease or urea carboxylase (hydrolyzing).

27. The device of claim 24 in which the hydrolyzing agent is urease.

28. A device for the determination of the specific gravity or osmolality of a liquid containing urea which comprises a carrier matrix incorporated with a hydrolyzing agent capable of hydrolyzing urea and microscapsules having osmotically fragile, semipermeable membrane walls, the walls encapsulating a solute and a coloring substance, the microcapsules being capable of releasing the encapsulated contents to produce a color change when subjected to a preselected osmotic gradient across said walls.

29. The device of claim 28 in which the hydrolyzing agent is an enzyme capable of hydrolyzing urea.

30. The device of claim 28 in which the hydrolyzing agent is urease or urea carboxylase (hydrolyzing).

31. The device of claim 28 in which the hydrolyzing agent is urease.

32. The device of claim 28 in which the microcapsules each enclose an inner phase of predetermined specific gravity, the inner phase comprising a solute and a coloring substance, the specific gravity of the inner phase being higher than that of the liquid containing urea, such that, upon contact with said liquid, hydrostatic pressure is produced within the microcapsules, thereby causing the release of the inner phase from the microcapsules, the density of the color produced by the release being inversely proportional to the specific gravity of said liquid.

33. The device of claim 32 in which the hydrolyzing agent is an enzyme capable of hydrolyzing urea.

34. The device of claim 32 in which the hydrolyzing agent is urease or urea carboxylase (hydrolyzing).

35. The device of claim 32 in which the hydrolyzing agent is urease.

* * * * *